US012303206B2

(12) United States Patent
Shin et al.

(10) Patent No.: US 12,303,206 B2
(45) Date of Patent: May 20, 2025

(54) METHOD AND APPARATUS FOR GENERATING VIRTUAL INTERNAL FIXTURE ON BASIS OF IMAGE REDUCTION

(71) Applicant: THE CATHOLIC UNIVERSITY OF KOREA INDUSTRY-ACADEMIC COOPERATION FOUNDATION, Seoul (KR)

(72) Inventors: Seung Han Shin, Seoul (KR); Yang Guk Chung, Seoul (KR); Do Kun Yoon, Suwon-si (KR); Moo Sub Kim, Gimhae-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 975 days.

(21) Appl. No.: 17/415,526

(22) PCT Filed: Dec. 23, 2019

(86) PCT No.: PCT/KR2019/018294
§ 371 (c)(1),
(2) Date: Jun. 17, 2021

(87) PCT Pub. No.: WO2020/149544
PCT Pub. Date: Jul. 23, 2020

(65) Prior Publication Data
US 2022/0054196 A1    Feb. 24, 2022

(30) Foreign Application Priority Data
Jan. 18, 2019   (KR) .................. 10-2019-0006877

(51) Int. Cl.
*A61B 34/10*    (2016.01)
*A61B 17/74*    (2006.01)
(Continued)

(52) U.S. Cl.
CPC ............ *A61B 34/10* (2016.02); *A61B 17/746* (2013.01); *A61B 17/80* (2013.01); *A61B 2017/568* (2013.01)

(58) Field of Classification Search
CPC ........... A61B 34/10; A61B 7/746; A61B 7/80; A61B 2017/568
(Continued)

(56) References Cited

U.S. PATENT DOCUMENTS 10,588,589 B2 *  3/2020  Bregman-Amitai ..... G06N 5/02
11,080,852 B2 *  8/2021  Liao ....................... G16H 30/20
(Continued)

FOREIGN PATENT DOCUMENTS

CN    108338828 A    7/2018
JP    3735751        1/2006
(Continued)

OTHER PUBLICATIONS

International Search Report—PCT/KR2019/018294 dated Apr. 7, 2020.

*Primary Examiner* — Gabriel I Garcia
(74) *Attorney, Agent, or Firm* — CANTOR COLBURN LLP

(57) ABSTRACT

Provided are a method and an apparatus for generating a virtual internal fixture on the basis of image reduction, the method including: recognizing positions and shapes of multiple fracture fragments in a medical fracture image including a fracture site; determining conformity of the multiple fracture fragments by analyzing the shapes of the multiple fracture fragments; performing image reduction of the frac-
(Continued)

ture site by moving the positions of the multiple fracture fragments on the basis of the conformity; and generating the virtual internal fixture for fixing the fracture site for which image reduction has been performed.

16 Claims, 4 Drawing Sheets

(51) Int. Cl.
*A61B 17/80* (2006.01)
*A61B 17/56* (2006.01)

(58) Field of Classification Search
USPC .......................................................... 382/128
See application file for complete search history.

(56) References Cited

U.S. PATENT DOCUMENTS

| | | | |
|---|---|---|---|
| 2014/0233820 A1* | 8/2014 | Wu | ...................... A61B 6/5211 |
| | | | 382/131 |
| 2014/0379038 A1 | 12/2014 | Dogramadzi et al. | |
| 2015/0328004 A1 | 11/2015 | Mafhouz | |
| 2016/0331463 A1 | 11/2016 | Notzli et al. | |
| 2020/0229783 A1* | 7/2020 | Jung | ...................... A61B 6/025 |
| 2020/0327660 A1* | 10/2020 | Katouzian | ................. G06T 7/11 |
| 2021/0256716 A1* | 8/2021 | Siewerdsen | ............... G06T 7/11 |

FOREIGN PATENT DOCUMENTS

| | | |
|---|---|---|
| JP | 2017507689 | 3/2017 |
| KR | 20100024457 | 3/2010 |
| KR | 20160091322 | 8/2016 |
| KR | 101694639 | 1/2017 |

* cited by examiner

FIG. 3
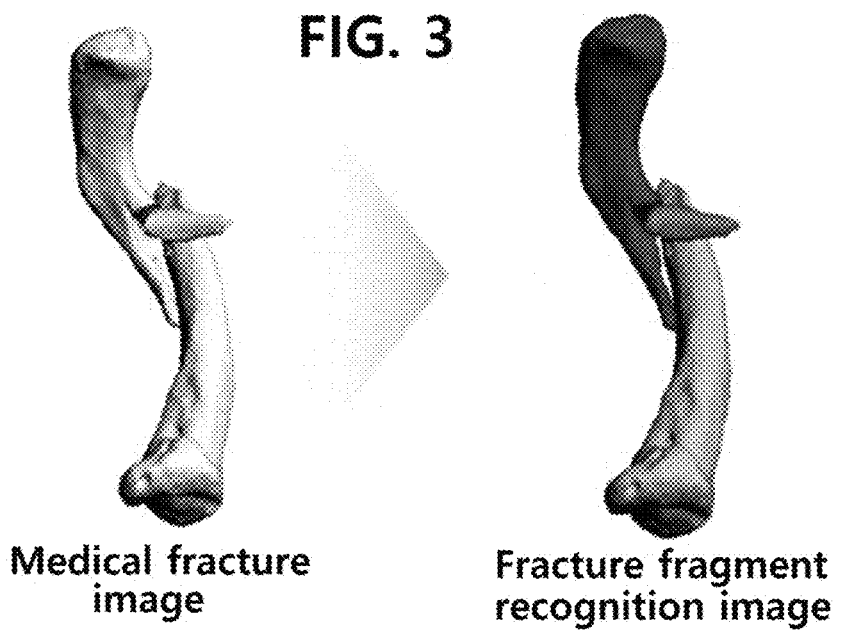
Medical fracture image → Fracture fragment recognition image
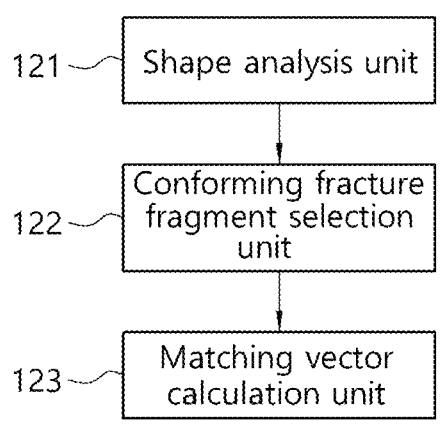
FIG. 4

Fracture fragment recognition image

Medical reduction image

FIG. 7

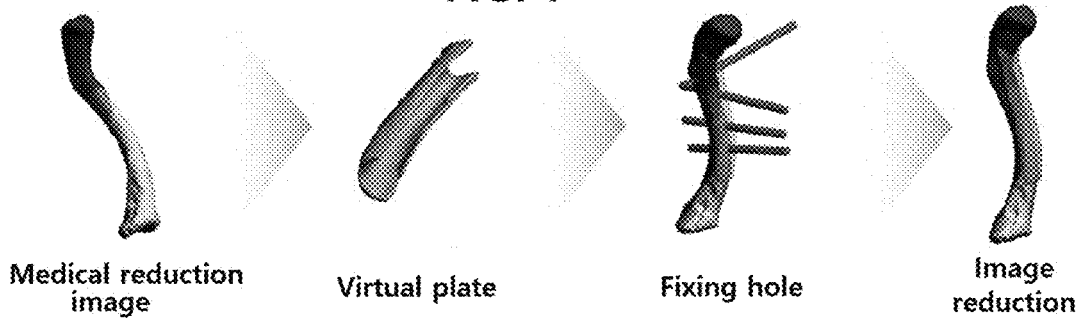

Medical reduction image → Virtual plate → Fixing hole → Image reduction

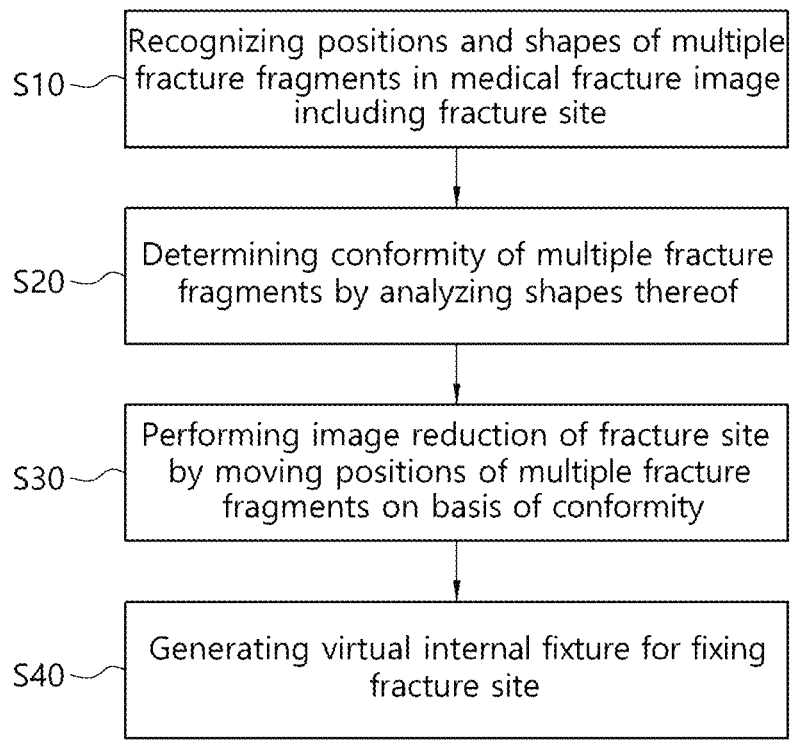

S10 — Recognizing positions and shapes of multiple fracture fragments in medical fracture image including fracture site S20 — Determining conformity of multiple fracture fragments by analyzing shapes thereof S30 — Performing image reduction of fracture site by moving positions of multiple fracture fragments on basis of conformity S40 — Generating virtual internal fixture for fixing fracture site

FIG. 8

METHOD AND APPARATUS FOR GENERATING VIRTUAL INTERNAL FIXTURE ON BASIS OF IMAGE REDUCTION

TECHNICAL FIELD

The present disclosure relates to a method and an apparatus for generating a virtual internal fixture on the basis of image reduction of fractured bones.

BACKGROUND ART

Fractures occur in various ways depending on the size and direction of stress, and fracture sites. Accordingly, the numbers, positions, and shapes of broken bone fragments, namely, fracture fragments, also vary.

To treat such various shapes of fractures, the skin and muscle tissue closest to the fracture site are incised and fracture fragments are arranged as similarly as possible to have their original positions and shapes before fracture. The arranged fracture fragments are fixed with plates and screws to prevent movement.

Herein, the operation of arranging fracture fragments to have their original positions and shapes before fracture is referred to as reduction. The operation of fixing fracture fragments with plates and screws is referred to as internal fixation. Plates and screws used for internal fixation, or human implants, such as metal pins or intramedullary nails, are referred to as internal fixtures. In such reduction and internal fixation procedures, the more the number of fracture fragments and the irregular shape, the higher the level of difficulty and the lower the success rate.

In the meantime, regarding a fracture, the numbers, positions, and shapes of fracture fragments vary according to the applied stress and a patient checks only an image of a fracture as a medical image for the first time, so it is impossible to know the original shape of the bone before fracture. The original shape of the fractured bone may be inferred from a mirror image of the opposite non-fractured bone (formed through mirroring), but this is not accurate because the left and right of the human bone are not completely the same.

So far, internal fixation procedures had to be performed with the original shapes of fractured bones being unknown, and for this reason, it was impossible to manufacture a personalized internal fixture, such as a plate that fits a patient's fractured bone. In a practical operation room, reduction has been performed grasping and moving fracture fragments manually and internal fixation has been performed using a commercialized plate. The problem is that the commercialized plate does not fit the reduced bone well.

Conventional plates and screws are standardized as commercialized medical devices. Considering the shape of bone of an average person, the conventional plates and screws are manufactured and sold in some different sizes and lengths based on an average shape. In a procedure, a patient's bone is actually reduced, plates of several standards are compared to the reduced bone, and the plate of which the shape and the size are the most similar to those of the reduced bone is used.

Even though the plates are standardized in average values, most plates do not fully conform with the shape of patient's bone thus making it difficult to perform the procedure. For example, a surface curvature or 3D twist degree of the bone does not fit a plate, or the position of a fixing hole of a plate does not fit a fracture fragment, so a screw cannot be inserted into the fracture fragment. In some cases, this makes internal fixation using a plate very difficult, and if internal fixation goes wrong, the original shape of bone may not be reconstructed or nonunion, which is failure of bone healing, may occur.

DISCLOSURE

Technical Problem

The present disclosure is directed to providing a method and an apparatus for generating a virtual internal fixture on the basis of image reduction, the method and the apparatus being capable of generating a virtual internal fixture on the basis of image reduction of bones, whereby a patient-personalized internal fixture can be manufactured.

In addition, the present disclosure is directed to providing a method and an apparatus for generating a virtual internal fixture on the basis of image reduction, the method and the apparatus being capable of adjusting a position and a direction of a fixing hole into which a fixing member is to be inserted, on the basis of image reduction of bones.

Technical Solution

According to an embodiment of the present disclosure, there is provided a method of generating a virtual internal fixture on the basis of image reduction, the method including: recognizing positions and shapes of multiple fracture fragments in a medical fracture image including a fracture site; determining conformity of the multiple fracture fragments by analyzing the shapes of the multiple fracture fragments; performing image reduction of the fracture site by moving the positions of the multiple fracture fragments on the basis of the conformity; and generating the virtual internal fixture for fixing the fracture site for which image reduction has been performed.

Herein, the recognizing of the positions and the shapes of the multiple fracture fragments may include: selecting multiple regions of interest from the medical fracture image; and extracting features of the multiple regions of interest.

In addition, at the recognizing of the positions and the shapes of the multiple fracture fragments, the shapes and the positions of the multiple fracture fragments may be recognized by analyzing the features of the multiple regions of interest.

In addition, the determining of the conformity of the multiple fracture fragments may include: analyzing ridges and fracture lines of the multiple fracture fragments; selecting a pair of conforming fracture fragments having the highest degree of conformity of the ridges and the fracture lines in the multiple fracture fragments; and calculating matching vectors of vertexes corresponding to each other included in the respective fracture lines of the pair of the conforming fracture fragments.

In addition, at the performing of image reduction of the fracture site, image reduction of the fracture site may be performed by moving at least one of the matching vectors of the vertexes corresponding to each other.

In addition, the generating of the virtual internal fixture may include: generating a plate body to be in contact with a surface of the fracture site for which image reduction has been performed; and forming a fixing hole for inserting a fixing member into the fracture site and the plate body.

In addition, at the forming of the fixing hole, a position and a direction in which the fixing member is to be inserted may be determined on the basis of the fracture site for which image reduction has been performed, and the fixing hole may be formed.

In addition, at the forming of the fixing hole, the fixing hole may be formed in a region other than a boundary between the multiple fracture fragments on the basis of the fracture site for which image reduction has been performed.

In addition, according to an embodiment of the present disclosure, there is provided an apparatus for generating a virtual internal fixture on the basis of image reduction, the apparatus including: a fracture fragment recognition unit recognizing positions and shapes of multiple fracture fragments in a medical fracture image including a fracture site; a conformity determination unit determining conformity of the multiple fracture fragments by analyzing the shapes of the multiple fracture fragments; an image reduction unit performing image reduction of the fracture site by moving the positions of the multiple fracture fragments on the basis of the conformity; and a virtual internal fixture generation unit generating the virtual internal fixture for fixing the fracture site for which image reduction has been performed.

Herein, the fracture fragment recognition unit may include: a region-of-interest selection unit selecting multiple regions of interest from the medical fracture image; and a feature extraction unit extracting features of the multiple regions of interest.

In addition, the fracture fragment recognition unit may recognize the shapes and the positions of the multiple fracture fragments by analyzing the features of the multiple regions of interest.

In addition, the conformity determination unit may include: a shape analysis unit analyzing ridges and fracture lines of the multiple fracture fragments; a conforming fracture fragment selection unit selecting a pair of conforming fracture fragments having the highest degree of conformity of the ridges and the fracture lines in the multiple fracture fragments; and a matching vector calculation unit calculating matching vectors of vertexes corresponding to each other included in the respective fracture lines of the pair of the conforming fracture fragments.

In addition, the image reduction unit may perform image reduction of the fracture site by moving at least one of the matching vectors of the vertexes corresponding to each other.

In addition, the virtual internal fixture generation unit may include: a plate body generation unit generating a plate body to be in contact with a surface of the fracture site for which image reduction has been performed; and a fixing hole formation unit forming a fixing hole for inserting a fixing member into the fracture site and the plate body.

In addition, the fixing hole formation unit may determine, on the basis of the fracture site for which image reduction has been performed, a position and a direction in which the fixing member is to be inserted, and may form the fixing hole.

In addition, the fixing hole formation unit may form the fixing hole in a region other than a boundary between the multiple fracture fragments on the basis of the fracture site for which image reduction has been performed.

Advantageous Effects

According to the present disclosure, the number, positions, and shapes of fracture fragments can be determined before the actual reduction procedure by performing image reduction, and the movement position of each fracture fragment for reduction can be determined. In addition, the shape of the bone when reduction procedure is ideally completed can be determined.

Through this, operator convenience can be improved, the time taken to make plans for reduction and internal fixation procedures can be shortened, and the accuracy of plans for reduction and internal fixation procedures can be increased. In addition, a patient can be provided with easy explanation of plans for personalized reduction and internal fixation procedures before reduction and internal fixation procedures.

In addition, according to the present disclosure, a virtual internal fixture is generated on the basis of image reduction of bones and an actual internal fixture is manufactured on the basis of the virtual internal fixture, so that a patient-personalized internal fixture can be manufactured. In addition, the position and direction of a fixing hole into which a fixing member is to be inserted can be adjusted on the basis of image reduction. Therefore, even in the case in which a procedure has a high level of difficulty, specifically, there is a number of fracture fragments or the shapes of the fracture fragments are irregular, such as comminuted fracture, a fixing member can be inserted into each fracture fragment. When fracture fragments are made to fit in a personalized plate, the original shape of the bone is naturally reconstructed, so the time taken to perform a procedure can be shortened, and as a result, the procedure success rate can be increased and the nonunion rate can be decreased.

Effects that may be obtained from the present disclosure will not be limited to only the above described effects. In addition, other effects which are not described herein will become apparent to those skilled in the art from the following description.

DESCRIPTION OF DRAWINGS

FIG. 3 is a diagram illustrating a process of generating a fracture fragment recognition image from a medical fracture image according to an embodiment of the present disclosure.

FIG. 4 is a detailed block diagram illustrating a conformity determination unit according to an embodiment of the present disclosure.

FIG. 7 is a diagram illustrating a process of generating a virtual internal fixture according to an embodiment of the present disclosure.

FIG. 8 is a flowchart illustrating a method of generating a virtual internal fixture on the basis of image reduction according to an embodiment of the present disclosure.

MODE FOR INVENTION

Figure 1:
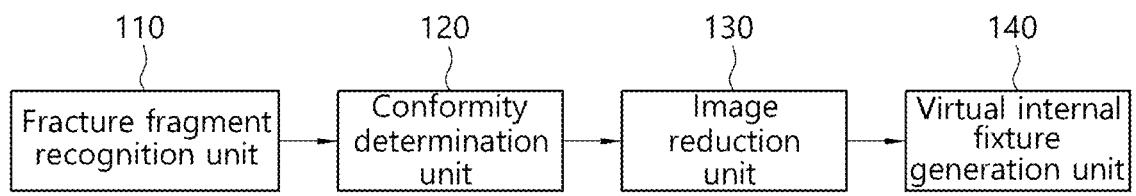
FIG. 1 is a schematic block diagram illustrating an apparatus for generating a virtual internal fixture on the basis of image reduction according to an embodiment of the present disclosure.

Hereinafter, embodiments of the present disclosure will be described in detail with reference to the drawings. In the accompanying drawings, it is to be noted that the same reference numerals are used for the same constituents.

Further, a detailed description of known functions and configurations will be omitted if it obscures the subject matter of the present disclosure.

In the embodiments of the present disclosure, each constituent may be composed of one or more sub-constituents. The electric, electronic, and mechanical functions that each constituent performs may be realized with various known elements or mechanical elements, such as electronic circuits, integrated circuits, and Application Specific Integrated Circuits (ASICs). Such functions may be separately realized, or may be realized with two or more thereof integrated into one.

FIG. 1 is a schematic block diagram illustrating an apparatus for generating a virtual internal fixture on the basis of image reduction according to an embodiment of the present disclosure.

As shown in FIG. 1, an apparatus for generating a virtual internal fixture on the basis of image reduction according to an embodiment of the present disclosure includes a fracture fragment recognition unit 110, a conformity determination unit 120, an image reduction unit 130, and a virtual internal fixture generation unit 140.

Figure 2:
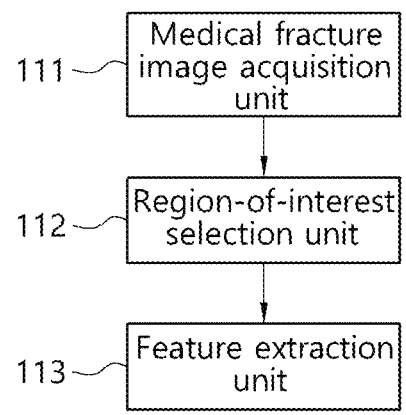
FIG. 2 is a detailed block diagram illustrating a fracture fragment recognition unit according to an embodiment of the present disclosure.

FIG. 2 is a detailed block diagram illustrating a fracture fragment recognition unit according to an embodiment of the present disclosure. FIG. 3 is a diagram illustrating a process of generating a fracture fragment recognition image from a medical fracture image according to an embodiment of the present disclosure.

Referring to FIG. 3, the fracture fragment recognition unit 110 recognizes positions and shapes of multiple fracture fragments from a medical fracture image including a fracture site.

As shown in FIG. 2, the fracture fragment recognition unit 110 may include a medical fracture image acquisition unit 111, a region-of-interest selection unit 112, and a feature extraction unit 113.

The medical fracture image acquisition unit 111 acquires a medical fracture image of a patient. That is, the medical fracture image acquisition unit 111 may receive a medical fracture image of a patient's fracture site acquired by an image acquisition device (not shown) through communication. Herein, the medical fracture image may be 2D and 3D medical image data acquired by various image acquisition devices including an X-ray image acquisition device, a computed tomography (CT) image acquisition device, and a magnetic resonance imaging (MRI) acquisition device.

The region-of-interest selection unit 112 selects multiple regions of interest from the medical fracture image of a patient acquired by the medical fracture image acquisition unit 111. Herein, a region of interest is a region in which a fracture fragment is highly likely to be positioned in a medical fracture image, and may be selected using various image analysis algorithms.

The feature extraction unit 113 extracts features of multiple regions of interest, and the fracture fragment recognition unit 114 recognizes shapes and positions of the multiple fracture fragments by analyzing the features of the multiple regions of interest.

Specifically, the fracture fragment recognition unit 114 may learn features of multiple fracture fragments in advance using a learning model, and may compare the learned features of the fracture fragments with features of regions of interest for a patient extracted by the feature extraction unit 113, thereby detecting shapes and positions of fracture fragments.

Figure 5:
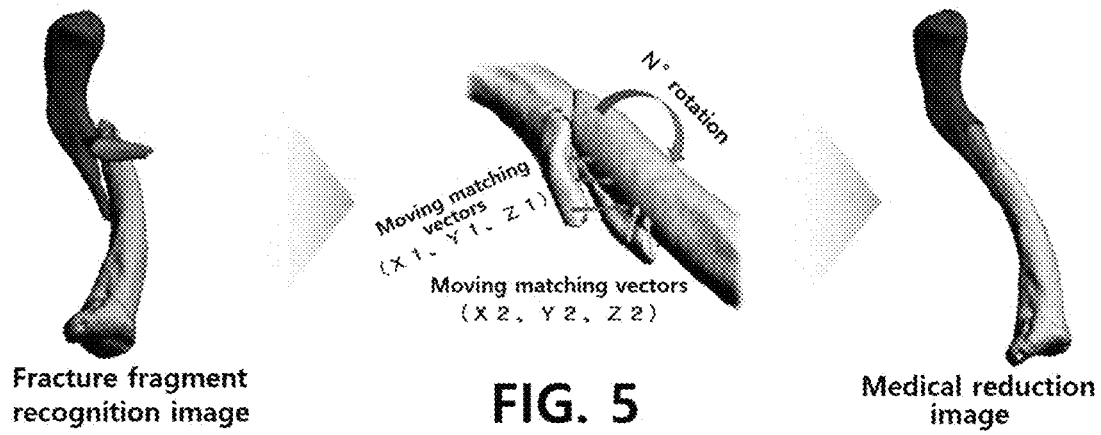
FIG. 5 is a diagram illustrating a process of changing a fracture fragment recognition image to a medical reduction image according to an embodiment of the present disclosure.

FIG. 4 is a detailed block diagram illustrating a conformity determination unit according to an embodiment of the present disclosure. FIG. 5 is a diagram illustrating a process of changing a fracture fragment recognition image to a medical reduction image according to an embodiment of the present disclosure.

Referring to FIGS. 4 and 5, the conformity determination unit 120 determines the conformity of multiple fracture fragments by analyzing the shapes of the multiple fracture fragments.

As shown in FIG. 4, the conformity determination unit 120 may include a shape analysis unit 121, a conforming fracture fragment selection unit 122, and a matching vector calculation unit 123.

The shape analysis unit 121 analyzes ridges and fracture lines of multiple fracture fragments. Herein, a ridge of a fracture fragment means a part exposed to the outside before fracture, and a fracture line of a fracture fragment means a part exposed to the outside after fracture. In the meantime, a ridge and a fracture line of a fracture fragment are expressions in the case in which a medical fracture image is 2D medical image data. In the case in which a medical fracture image is 3D medical image data, a ridge and a fracture line of a fracture fragment may be expressed as a ridge surface and a fracture surface of a fracture fragment.

The conforming fracture fragment selection unit 122 selects a pair of conforming fracture fragments having the highest degree of conformity of the ridges and the fracture lines in multiple fracture fragments.

That is, the conforming fracture fragment selection unit 122 may learn ridges of multiple non-fractured normal bones in advance using a learning model. In addition, multiple fracture fragments are made conforming, the ridges of the conforming fracture fragments are compared to the learned ridge of the normal bone, and the conformity of the ridges of the fracture fragments is determined.

In addition, the conforming fracture fragment selection unit 122 makes multiple fracture fragments conforming and checks whether the fracture lines of the conforming fracture fragments fit well, thereby determining the conformity of the fracture lines of the fracture fragments.

In this way, the conforming fracture fragment selection unit 122 determines the conformity of the ridges and the fracture lines of multiple fracture fragments, and selects a pair of conforming fracture fragments.

In the meantime, in the case of simple fracture, one pair of conforming fracture fragments is selected, but in the case of comminuted fracture, multiple pairs of conforming fracture fragments may be selected.

The matching vector calculation unit 123 selects vertexes corresponding to each other included in the respective fracture lines of a pair of conforming fracture fragments, and calculates matching vectors of the selected vertexes. Herein, in the case in which a medical fracture image is 2D medical image data, a matching vector is composed of the x coordinate and the y coordinate. In the case in which a medical fracture image is 3D medical image data, a matching vector is composed of the x coordinate, the y coordinate, and the z coordinate.

The image reduction unit 130 performs image reduction of the fracture site by moving the positions of the multiple fracture fragments on the basis of the conformity determined by the conformity determination unit 120. That is, the image reduction unit 130 performs image reduction of the fracture site by moving the positions of a pair of conforming fracture fragments selected by the conforming fracture fragment selection unit 122.

Specifically, the image reduction unit 130 performs image reduction of the fracture site by moving at least one of the matching vectors of the vertexes corresponding to each other calculated by the matching vector calculation unit 123. For example, image reduction of the fracture site may be performed by moving a matching vector of any one of the vertexes corresponding to each other to a matching vector of another one of the vertexes. In such movement process, the conforming fracture fragment may be moved, rotating by a particular angle.

Alternatively, the image reduction unit 130 may perform image reduction of the fracture site in such a manner that the operator moves the positions of the multiple fracture fragments manually in the image on the basis of the conformity determined by the conformity determination unit 120. That is, the operator moves the positions of multiple fracture fragments in such a manner that the operator clicks on a fracture fragment in the image using a mouse and drags the fracture fragment to a position to which the fracture fragment is to move, thereby performing image reduction of the fracture site.

As described above, the apparatus for generating a virtual internal fixture on the basis of image reduction according to the embodiment of the present disclosure is able to determine the number, positions, and shapes of fracture fragments before the actual reduction procedure by performing image reduction, and is able to determine the movement position of each fracture fragment for reduction. In addition, the shape of the bone when reduction procedure is ideally completed can be determined.

Through this, operator convenience can be improved, the time taken to make plans for reduction and internal fixation procedures can be shortened, and the accuracy of plans for reduction and internal fixation procedures can be increased. In addition, a patient can be provided with easy explanation of plans for personalized reduction and internal fixation procedures before reduction and internal fixation procedures.

Figure 6:
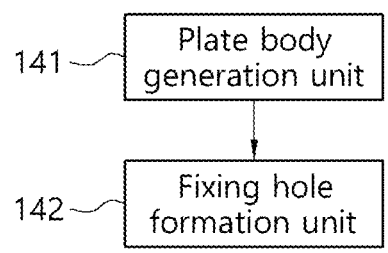
FIG. 6 is a detailed block diagram illustrating a virtual internal fixture generation unit according to an embodiment of the present disclosure.

FIG. 6 is a detailed block diagram illustrating a virtual internal fixture generation unit according to an embodiment of the present disclosure. FIG. 7 is a diagram illustrating a process of generating a virtual internal fixture according to an embodiment of the present disclosure.

Referring to FIG. 7, the virtual internal fixture generation unit 140 generates a virtual internal fixture for fixing the fracture site for which image reduction has been performed. Herein, the virtual internal fixture is an image of a virtual internal fixture that is simulated as an image before an actual internal fixture for fixing an actually reduced fracture site is manufacture.

Herein, the virtual internal fixture may be at least one among a virtual plate, a virtual metal pin, and a virtual intramedullary nail. Hereinafter, a case in which a virtual internal fixture is a virtual plate will be described as an example, but no limitation thereto is imposed.

Specifically, as shown in FIG. 6, the virtual internal fixture generation unit 140 may include a plate body generation unit 141 and a fixing hole formation unit 142.

The plate body generation unit 141 generates a plate body that is to be in contact with the surface of the fracture site for which image reduction has been performed. Herein, the plate body may be formed in the shape surrounding the bone of the fracture site.

In the meantime, in order to fix the plate body to the fracture site, a particular fixing member (for example, a screw) is required, and the plate body needs to be provided a fixing hole formed therein so that the fixing member is to be inserted into the fracture site and the plate body.

To this end, the fixing hole formation unit 142 forms a fixing hole for inserting the fixing member into the fracture site and the plate body.

In particular, the fixing hole formation unit 142 determines the position and direction in which the fixing member is to be inserted, on the basis of the fracture site for which image reduction has been performed, and forms the fixing hole.

Specifically, the fixing hole formation unit 142 forms, on the basis of the fracture site for which image reduction has been performed, a fixing hole in a region other than the boundary between the multiple fracture fragments. This may solve the problem that a plate body is not firmly fixed to a fracture site because a fixing hole is formed in a region of the boundary between multiple fracture fragments and a fixing member is inserted into the fixing hole.

As described above, the apparatus for generating a virtual internal fixture on the basis of image reduction according to the embodiment of the present disclosure generates a virtual internal fixture on the basis of image reduction of bones and an actual internal fixture is manufactured on the basis of the virtual internal fixture, so that a patient-personalized internal fixture can be manufactured. In addition, the position and direction of a fixing hole into which a fixing member is to be inserted can be adjusted on the basis of image reduction. Therefore, even in the case in which a procedure has a high level of difficulty, specifically, there is a number of fracture fragments or the shapes of the fracture fragments are irregular, such as comminuted fracture, a fixing member can be inserted into each fracture fragment. When fracture fragments are made to fit in a personalized plate, the original shape of the bone is naturally reconstructed, so the time taken to perform a procedure can be shortened, and as a result, the procedure success rate can be increased and the nonunion rate can be decreased.

FIG. 8 is a flowchart illustrating a method of generating a virtual internal fixture on the basis of image reduction according to an embodiment of the present disclosure.

Hereinafter, a method of generating a virtual internal fixture on the basis of image reduction according to an embodiment of the present disclosure will be described with reference to FIGS. 1 to 8. The same details as those of the apparatus for generating a virtual internal fixture on the basis of image reduction according to the above-described embodiment of the present disclosure will be omitted.

As shown in FIG. 8, a method of generating a virtual internal fixture on the basis of image reduction according to an embodiment of the present disclosure includes: recognizing positions and shapes of multiple fracture fragments in a medical fracture image including a fracture site at step S10; determining conformity of the multiple fracture fragments by analyzing the shapes of the multiple fracture fragments at step S20; performing image reduction of the fracture site by moving the positions of the multiple fracture fragments on the basis of the conformity at step S30; and generating the virtual internal fixture for fixing the fracture site for which image reduction has been performed at step S40.

The recognizing of the positions and the shapes of the multiple fracture fragments at step S10 may include: selecting multiple regions of interest from the medical fracture image; and extracting features of the multiple regions of interest.

Herein, at the recognizing of the positions and the shapes of the multiple fracture fragments at step S10, the shapes and the positions of the multiple fracture fragments may be recognized by analyzing the features of the multiple regions of interest.

The determining of the conformity of the multiple fracture fragments at step S20 may include: analyzing ridges and fracture lines of the multiple fracture fragments; selecting a pair of conforming fracture fragments having the highest degree of conformity of the ridges and the fracture lines in the multiple fracture fragments; and calculating matching vectors of vertexes corresponding to each other included in the respective fracture lines of the pair of the conforming fracture fragments.

At the performing of image reduction of the fracture site at step S30, image reduction of the fracture site may be performed by moving at least one of the matching vectors of the vertexes corresponding to each other.

Alternatively, at the performing of image reduction of the fracture site at step S30, image reduction of the fracture site may be performed in such a manner that the operator moves the positions of the multiple fracture fragments manually in the image on the basis of the conformity of the multiple fracture fragments. That is, the operator moves the positions of multiple fracture fragments in such a manner that the operator clicks on a fracture fragment in the image using a mouse and drags the fracture fragment to a position to which the fracture fragment is to move, thereby performing image reduction of the fracture site.

As described above, the method of generating a virtual internal fixture on the basis of image reduction according to the embodiment of the present disclosure is able to determine the number, positions, and shapes of fracture fragments before the actual reduction procedure by performing image reduction, and is able to determine the movement position of each fracture fragment for reduction. In addition, the shape of the bone when reduction procedure is ideally completed can be determined.

Through this, operator convenience can be improved, the time taken to make plans for reduction and internal fixation procedures can be shortened, and the accuracy of plans for reduction and internal fixation procedures can be increased. In addition, a patient can be provided with easy explanation of plans for personalized reduction and internal fixation procedures before reduction and internal fixation procedures.

The generating of the virtual internal fixture at step S40 may include: generating a plate body to be in contact with a surface of the fracture site for which image reduction has been performed; and forming a fixing hole for inserting a fixing member into the fracture site and the plate body.

Herein, at the forming of the fixing hole, a position and a direction in which the fixing member is to be inserted may be determined on the basis of the fracture site for which image reduction has been performed, and the fixing hole may be formed.

In addition, at the forming of the fixing hole, the fixing hole may be formed in a region other than a boundary between the multiple fracture fragments on the basis of the fracture site for which image reduction has been performed.

As described above, the method of generating a virtual internal fixture on the basis of image reduction according to the embodiment of the present disclosure generates a virtual internal fixture on the basis of image reduction of bones and an actual internal fixture is manufactured on the basis of the virtual internal fixture, so that a patient-personalized internal fixture can be manufactured. In addition, the position and direction of a fixing hole into which a fixing member is to be inserted can be adjusted on the basis of image reduction.

Therefore, even in the case in which a procedure has a high level of difficulty, specifically, there is a number of fracture fragments or the shapes of the fracture fragments are irregular, such as comminuted fracture, a fixing member can be inserted into each fracture fragment. When fracture fragments are made to fit in a personalized plate, the original shape of the bone is naturally reconstructed, so the time taken to perform a procedure can be shortened, and as a result, the procedure success rate can be increased and the nonunion rate can be decreased.

In the meantime, the embodiments of the present disclosure described in the specification and drawings are suggested as a specific example to easily describe the present disclosure and to help understanding of the present disclosure, and do not limit the scope of the present disclosure. That is, it is obvious to those skilled in the art that other modifications based on the technical idea of the present disclosure may be implemented.

The invention claimed is:

1. A method of generating a virtual internal fixture on the basis of image reduction, the method comprising:
   recognizing positions and shapes of multiple fracture fragments in a medical fracture image including a fracture site;
   determining conformity of the multiple fracture fragments by analyzing the shapes of the multiple fracture fragments;
   performing image reduction of the fracture site by moving the positions of the multiple fracture fragments on the basis of the conformity; and
   generating the virtual internal fixture for fixing the fracture site for which image reduction has been performed.

2. The method of claim 1, wherein the recognizing of the positions and the shapes of the multiple fracture fragments comprises:
   selecting multiple regions of interest from the medical fracture image; and
   extracting features of the multiple regions of interest.

3. The method of claim 2, wherein at the recognizing of the positions and the shapes of the multiple fracture fragments, the shapes and the positions of the multiple fracture fragments are recognized by analyzing the features of the multiple regions of interest.

4. The method of claim 1, wherein the determining of the conformity of the multiple fracture fragments comprises:
   analyzing ridges and fracture lines of the multiple fracture fragments;
   selecting a pair of conforming fracture fragments having the highest degree of conformity of the ridges and the fracture lines in the multiple fracture fragments; and
   calculating matching vectors of vertexes corresponding to each other included in the respective fracture lines of the pair of the conforming fracture fragments.

5. The method of claim 4, wherein at the performing of image reduction of the fracture site, image reduction of the fracture site is performed by moving at least one of the matching vectors of the vertexes corresponding to each other.

6. The method of claim 1, wherein the generating of the virtual internal fixture comprises:
   generating a plate body to be in contact with a surface of the fracture site for which image reduction has been performed; and
   forming a fixing hole for inserting a fixing member into the fracture site and the plate body.

7. The method of claim 6, wherein at the forming of the fixing hole, a position and a direction in which the fixing member is to be inserted are determined on the basis of the fracture site for which image reduction has been performed, and the fixing hole is formed.

8. The method of claim 6, wherein at the forming of the fixing hole, the fixing hole is formed in a region other than a boundary between the multiple fracture fragments on the basis of the fracture site for which image reduction has been performed.

9. An apparatus for generating a virtual internal fixture on the basis of image reduction, the apparatus comprising:
- a fracture fragment recognition unit recognizing positions and shapes of multiple fracture fragments in a medical fracture image including a fracture site;
- a conformity determination unit determining conformity of the multiple fracture fragments by analyzing the shapes of the multiple fracture fragments;
- an image reduction unit performing image reduction of the fracture site by moving the positions of the multiple fracture fragments on the basis of the conformity; and
- a virtual internal fixture generation unit generating the virtual internal fixture for fixing the fracture site for which image reduction has been performed.

10. The apparatus of claim 9, wherein the fracture fragment recognition unit comprises:
- a region-of-interest selection unit selecting multiple regions of interest from the medical fracture image; and
- a feature extraction unit extracting features of the multiple regions of interest.

11. The apparatus of claim 10, wherein the fracture fragment recognition unit recognizes the shapes and the positions of the multiple fracture fragments by analyzing the features of the multiple regions of interest.

12. The apparatus of claim 9, wherein the conformity determination unit comprises:
- a shape analysis unit analyzing ridges and fracture lines of the multiple fracture fragments;
- a conforming fracture fragment selection unit selecting a pair of conforming fracture fragments having the highest degree of conformity of the ridges and the fracture lines in the multiple fracture fragments; and
- a matching vector calculation unit calculating matching vectors of vertexes corresponding to each other included in the respective fracture lines of the pair of the conforming fracture fragments.

13. The apparatus of claim 12, wherein the image reduction unit performs image reduction of the fracture site by moving at least one of the matching vectors of the vertexes corresponding to each other.

14. The apparatus of claim 9, wherein the virtual internal fixture generation unit comprises:
- a plate body generation unit generating a plate body to be in contact with a surface of the fracture site for which image reduction has been performed; and
- a fixing hole formation unit forming a fixing hole for inserting a fixing member into the fracture site and the plate body.

15. The apparatus of claim 14, wherein the fixing hole formation unit determines, on the basis of the fracture site for which image reduction has been performed, a position and a direction in which the fixing member is to be inserted, and forms the fixing hole.

16. The apparatus of claim 14, wherein the fixing hole formation unit forms the fixing hole in a region other than a boundary between the multiple fracture fragments on the basis of the fracture site for which image reduction has been performed.

* * * * *